(12) United States Patent
Izui et al.

(10) Patent No.: US 7,247,459 B1
(45) Date of Patent: Jul. 24, 2007

(54) L-GLUTAMIC ACID PRODUCING BACTERIUM AND PROCESS FOR PRODUCING L-GLUTAMIC ACID

(75) Inventors: Hiroshi Izui, Kawasaki (JP); Mika Moriya, Kawasaki (JP); Yoshihiko Hara, Kawasaki (JP); Hisao Ito, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/419,611

(22) Filed: Oct. 18, 1999

(30) Foreign Application Priority Data

Oct. 19, 1998 (JP) .................. 10-297350

(51) Int. Cl.
*C12P 13/14* (2006.01)
*C12N 9/10* (2006.01)
*C12N 1/20* (2006.01)
*C12N 15/00* (2006.01)
*C07H 21/04* (2006.01)

(52) U.S. Cl. .............. 435/110; 435/106; 435/183; 435/193; 435/252.33; 435/320.1; 536/23.2

(58) Field of Classification Search ............. 435/252.3, 435/106, 110, 183, 193, 252.33, 320.1; 536/23.2
See application file for complete search history.

(56) References Cited

U.S. PATENT DOCUMENTS 5,908,768 A 6/1999 Ono et al. .................. 435/110

6,197,559 B1 * 3/2001 Moriya et al. ............. 435/110

FOREIGN PATENT DOCUMENTS

| EP | 0 952 221 | 10/1999 |
|----|-----------|---------|
| JP | 32-9393 S | 12/1957 |
| JP | 63119688 A | 5/1988 |
| JP | 63-214189 | 9/1988 |
| JP | 63214189 | * 9/1988 |
| JP | 4-365493 | 12/1992 |
| WO | 0 670 370 | 9/1995 |
| WO | 97 08294 | 3/1997 |
| WO | WO97/08294 | 3/1997 |

OTHER PUBLICATIONS

Skillman et al. Microbiology. Aug. 1998;144 ( Pt 8):2095-101.*
Eikmanns et al. Microbiology. Aug. 1994;140 ( Pt 8):1817-28.*
NCBI Taxonomy Browser, Corynebacteriaum glutamicum, printed on Oct. 11, 2005.*

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

L-glutamic acid is produced by culturing in a medium a microorganism belonging to enterobacteria and having L-glutamic acid productivity, into which a citrate synthase gene derived from a coryneform bacterium is introduced to produce and accumulate L-glutamic acid in the medium and collecting the L-glutamic acid from the medium.

19 Claims, 2 Drawing Sheets

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: synthetic DNA

<400> SEQUENCE: 1
gtcgacaata gccygaatct gttctggtcg                30

```
<210> SEQ ID NO 2
<211> LENGTH: 30
<212> TYPE: DNA
<213> ORGANISM: Artificial Sequence
<220> FEATURE:
<223> OTHER INFORMATION: synthetic DNA

<400> SEQUENCE: 2
aagcttatcg acgctcccct ccccaccgtt                                            30
```

L-GLUTAMIC ACID PRODUCING BACTERIUM AND PROCESS FOR PRODUCING L-GLUTAMIC ACID

TECHNICAL FIELD

The present invention relates to a new L-glutamic acid producing bacterium and a process for producing L-glutamic acid by a fermentation method using the same. L-glutamic acid is an important amino acid as a food, medicament or the like.

BACKGROUND ART

Heretofore, L-glutamic acid has been produced by a fermentation method using mainly so-called a coryneform L-glutamic acid producing bacterium belonging to the genus *Brevibacterium*, *Corynebacterium* or *Microbacterium* or a variant thereof (Amino Acid Fermentation, Gakkai Shuppan Center, pp. 195-215, 1986). Known processes for producing L-glutamic acid by a fermentation method using other strains include one using a microorganism belonging to the genus *Bacillus, Streptomyces* or *Penicillium* (U.S. Pat. No. 3,220,929), one using a microorganism belonging to the genus *Pseudomonas, Arthrobacter, Serratia* or *Candida* (U.S. Pat. No. 3,563,857), one using a microorganism such as a bacterium belonging to the genus *Bacillus, Pseudomonas, Serratia* or Aerobacter aerogenes (currently *Enterobacter aerogenes*) (Examined Japanese Patent Publication No. 32-9393), one using a mutant of *Escherichia coli* (Japanese Laid-open Patent Application No. 5-244970) and the like.

The productivity of L-glutamic acid has been considerably improved by the breeding of the above microorganisms or the improvement of the production processes. To meet growing demand for L-glutamic acid, the development of a more inexpensive and efficient process for producing L-glutamic acid is desired.

In view of the above situation, the inventors of the present invention has investigated and studied microorganisms having L-glutamic acid productivity broadly. As a result, it has been found that a microorganism having high L-glutamic acid productivity can be obtained by increasing the activity of an enzyme which catalyzes the L-glutamic acid biosynthesis reaction (citrate synthase, phosphoenolpyruvate carboxylase, glutamate dehydrogenase) of a microorganism belonging to the genus *Enterobacter, Serratia, Klebsiella* or *Erwinia* (Japanese Laid-open Patent Application Nos. 10-224909 and 10-297129).

The inventors have also found that a microorganism having high L-glutamic acid productivity is obtained by enhancing the activity of each of these enzymes by introducing a gene coding citrate synthase (hereinafter sometimes abbreviated as "CS") and phosphoenolpyruvate carboxylase derived from the genus *Escherichia* into a valine sensitive strain belonging to the genus *Escherichia* (WO 97/08294).

Meanwhile, it has been reported that the introduction of a gene (CS gene) coding citrate synthase derived from *Escherichia coli* or *Corynebacterium glutamicum* is effective in improving the L-glutamic acid productivity of *Corynebacterium* or *Brevibacterium* (Examined Japanese Patent Publication No. 7-121228). When these coryneform bacteria were used as a host, the introduction of a CS gene derived from *Corynebacterium glutamicum* of the same species as the host showed a slightly higher effect than the introduction of a CS gene derived from *Escherichia coli* but there was not seen a marked difference between them.

As described above, it has been known that a CS gene is introduced into various microorganisms to improve L-glutamic acid productivity. However, there has not been known an example where a CS gene derived from a coryneform bacterium is introduced into a microorganism belonging to enterobacteria such as a bacterium belonging to the genus *Escherichia*.

SUMMARY OF THE INVENTION

It is an object of the present invention to find a new L-glutamic acid producing bacterium having L-glutamic acid productivity in order to develop an inexpensive and efficient process for producing L-glutamic acid.

The inventors of the present invention have bred enterobacteria by introducing a gene to improve their productivity of L-glutamic acid. Generally, it has been considered that a better effect is obtained by using a endogenous gene of a host or a gene derived from a microorganism which is a relative of the host than by introducing a heterogeneous gene when the host has a target gene for the breeding of a microorganism by gene amplification. However, the inventors of the present invention have found it much more effective, for enterobacteria, in improving the L-glutamic acid productivity of a microorganism to introduce a CS gene derived from a coryneform bacterium than to introduce a CS gene derived from a microorganism of the same species as the enterobacteria. The present invention has been accomplished based on this finding.

That is, the present invention provides:

(1) a microorganism belonging to enterobacteria and having L-glutamic acid productivity, into which a citrate synthase gene derived from a coryneform bacterium is introduced, (2) the microorganism of above (1) wherein the coryneform bacterium is *Brevibacterium lactofermentum*, (3) the microorganism of (1) or (2) wherein the microorganism belonging to enterobacteria which a bacterium belonging to the genus *Enterobacter* or *Klebsiella*, (4) the microorganism of (3) wherein the bacterium belongs to *Enterobacter* agromellans or *Klebsiella planticola*, and (5) a process for producing L-glutamic acid comprising the steps of culturing the microorganism of any one of the above (1) to (4) in a liquid medium to produce and accumulate L-glutamic acid in the medium and collecting the L-glutamic acid from the medium.

DETAILED DESCRIPTION OF THE INVENTION

The present invention will be described in detail below.

<1> Microorganism of the Present Invention

The microorganism belonging to enterobacteria of the present invention is not particularly limited if it belongs to enterobacteria which can be conferred or improved L-glutamic acid productivity by introducing a CS gene derived from a coryneform bacterium. The microorganism is exemplified by a bacterium belonging to the genus *Enterobacter, Klebsiella, Serratia, Erwinia, Pantoea* or *Escherichia*. Out of these, bacteria belonging to the genus *Enterobacter* or *Klebsiella* are preferred. Illustrative examples of the bacteria are described below but the microorganism of the present invention is not limited to these examples.

Examples of the microorganism belonging to the genus *Enterobacter* that can be used for the present invention are listed below.

*Enterobacter agglomerans*
*Enterobacter aerogenes*
*Enterobacter amnigenus*
*Enterobacter asburiae*
*Enterobacter cloacae*
*Enterobacter dissolvens*
*Enterobacter gergoviae*
*Enterobacter hormaechei*
*Enterobacter intermedius*
*Enterobacter nimipressuralis*
*Enterobacter sakazakii*
*Enterobacter taylorae*

More preferably, those bacterial strains listed bel ow can be mentioned:

*Enterobacter agglomerans* AJ13355
*Serratia liquefacience* ATCC 14460

The *Enterobacter agglomerans* AJ13355 was deposited at the National Institute of Bioscience and Human-Technology, Agency of Industrial Science and Technology, Ministry of International Trade and Industry on Feb. 19, 1998, and received an accession number of FERM P-16644, and then transferred to an international deposit under the Budapest Treaty on Jan. 11, 1999, and received an accession number of FERM BP-6614. The *Enterobacter agglomerans* ATCC 12287, and the *Serratia liquefacience* ATCC 14460 can be distributed from ATCC.

The *Enterobacter agglomerans*. AJ13355 strain is a strain isolated from soil in Iwata-shi, Shizuoka, Japan.

Physiological properties of AJ13355 are as follows.

(1) Gram stain: Negative (2) Aerophobicity: Facultative anaerobe (3) Catalase: Positive (4) Oxidase: Negative (5) Nitrate reduction ability: Negative (6) Voges-Proskauer reaction: Positive (7) Methyl Red test: Negative (8) Urease: Negative (9) Indole production: Positive (10) Motility: Present (11) Hydrogen sulfide production in TSI culture medium: Slightly active (12) β-Galactosidase: Positive (13) Sugar assimilability:
Arabinose: Positive
Sucrose: Positive
Lactose: Positive
Xylose: Positive
Sorbitol: Positive
Inositol: Positive
Trehalose: Positive
Maltose: Positive
Melibiose: Positive
Adonitol: Negative
Raffinose: Positive
Salicin: Negative
Melibiose: Positive (14) Glycerose assimilability: Positive (15) organic acid assimilability:
Citric acid: Positive
Tartaric acid: Negative
Gluconic acid: Positive
Acetic acid: Positive
Malonic acid: Negative (16) Arginine dehydratase: Negative (17) Ornithine decarboxylase: Negative (18) Lysine decarboxylase: Negative (19) Phenylalanine deaminase: Negative (20) Chromogenesis: Yellow (21) Gelatin liquefaction ability: Positive (22) Growth pH: Not good growth at pH 4, good growth at pH 4.5-7

(23) Growth temperature: Good growth at 25° C., good growth at 30° C., good growth at 37° C., growth is possible at 42° C., no growth at 45° C.

From these bacteriological properties, AJ13355 is determined to be *Enterobacter agglomerans*.

Examples of the microorganism belonging to the genus *Klebsiella* that can be used for the present invention are listed below.

*Klebsiella planticola*
*Klebsiella terrigena*

More preferably, the examples of the microorganism include *Klebsiella planticola* AJ13399.

The *Klebsiella planticola* AJ13399 was deposited at the National Institute of Bioscience and Human-Technology, Agency of Industrial Science and Technology, Ministry of International Trade and Industry on Feb. 19, 1998, and received an accession number of FERM P-16646, and then transferred to an international deposit under the Budapest Treaty on Jan. 11, 1999, and received an accession number of FERM BP-6616.

The *Klebsiella planticola* AJ13399 strain is a strain isolated from soil in Sapporo-shi, Hokkaido, Japan.

Physiological properties of AJ13399 are as follows.

(1) Cell morphology: Rod-shaped (2) Motility: Absent (3) Spore formation: Absent (4) Colony morphology on LabM nutrient agar: Circular, smooth surface, cream in color, even, raised, and glistening (5) Glucose OF test: Positive for fermentability (6) Gram stain: Negative (7) Aerophobicity: Facultative anaerobe (8) Catalase: Positive (9) Oxidase: Negative (10) Urease: Positive (11) Cytochrome oxidase: Negative (12) β-Galactosidase: Positive (13) Arginine dehydratase: Negative (14) Ornithine decarboxylase: Negative (15) Lysine decarboxylase: Positive (16) Tryptophan deaminase: Negative (17) Voges-Proskauer reaction: Positive (18) Indole production: Positive (19) Hydrogen sulfide production in TSI culture medium: Negative (20) Citric acid assimilability: Positive (21) m-Hydroxybenzene acid assimilability: Negative (22) Gelatin liquefaction ability: Negative (23) Production of acid from sugar
  Glucose: Positive
  Mannitol: Positive
  Rhamnose: Positive
  Arabinose: Positive
  Sucrose: Positive
  Sorbitol: Positive
  Inositol: Positive
  Melibiose: Positive
  Amygdalin: Positive
  Adonitol-peptone-water: Positive
  Cellobiose-peptone-water: Positive
  Dulcitol-peptone-water: Negative
  Raffinose-peptone-water: Positive (24) Growth temperature: Good growth at 37° C., no growth at 45° C.

From these bacteriological properties, AJ13399 is determined to be *Klebsiella planticola*.

Examples of the microorganism belonging to the genus *Serratia* that can be used for the present invention are listed below.
  *Serratia liquefacience*
  *Serratia entomophila*
  *Serratia ficaria*
  *Serratia fonticola*
  *Serratia grimesii*
  *Serratia proteamaculans*
  *Serratia odorifera*
  *Serratia plymuthica*
  *Serratia rubidaea*

More preferably, *Serratia liquefacience* ATCC 14460 may be exemplified. *Serratia liquefacience* ATCC 14460 can be distributed from ATCC.

Examples of the microorganism belonging to the genus *Erwinia* that can be used for the present invention are listed below.
  *Erwinia herbicola* (now classified as *Pantoea agglomerans*)
  *Erwinia ananas*
  *Erwinia cacticida*
  *Erwinia chrysanthemi*
  *Erwinia mallotivora*
  *Erwinia persicinus*
  *Erwinia psidii*
  *Erwinia quercina*
  *Erwinia rhapontici*
  *Erwinia rubrifaciens*
  *Erwinia salicis*
  *Erwinia uredovora*

More preferably, *Erwinia herbicola* IAM1595 (*Pantoea agglomerans* AJ2666) is exemplified. *Erwinia herbicola* IAM1595 can be distributed from the Institute of Molecular and Cellular Biosciences, the University of Tokyo. It should be noted that in the "Bergey's Manual of Determinative Bacteriology, ninth edition," *Erwinia helbicola* is not described and microorganisms which have been classified as *Erwinia helbicola* are classified as *Pantoea agglomerans*. Microorganisms which have been classified as *Erwinia helbicola* are now classified as *Pantoea agglomerans*. Thus the microorganisms belonging to genus *Erwinia* and the microorganisms belonging to the genus *Pantoea* are closely related to each other. Therefore, any of microorganisms belonging to the genus *Pantoea* can be used as welle as the microorganisms belonging to the genus *Erwinia*. Such microorganisms include *Pantoea agglomerans* and *Pantoea dispersa*. *Erwinia herbicola* IAM1595 is designated as *Pantoea agglomerans* AJ2666, and was deposited at the National Institute of Bioscience and Human-Technology, Agency of Industrial Science and Technology, Ministry of International Trade and Industry on Feb. 25, 1999 as an international deposition under the Budapest Treaty and received an accession number of FERM BP-6660.

Examples of the microorganism belonging to the genus *Escherichia* that can be used for the present invention include *Escherichia coli*.

More preferably, *Escherichia coli* having valine resistance, for example, the following strains may be exemplified.
  *Eschericha coli* K-12 (ATCC10798)
  *Escherichia coli* B (ATCC11303)
  *Escherichia coli* W (ATCC9637)

*Eschericha coil* K-12 (ATCC10798), *Escherichia coli* B (ATCC11303) and *Escherichia coli* W (ATCC9637) can be distributed from ATCC.

It should be noted that, the sugar metabolism by bacteria belonging to the genera *Enterobacter, Klebsiella, Serratia, Erwinia, Pantoea* and *Escherichia* such as those mentioned above is achieved via the Embden-Meyerhof pathway, and pyruvic acid produced in that pathway is oxidized in the tricarboxylic acid cycle as for aerobic condition. L-glutamic acid is biosynthesized from α-ketoglutaric acid which is an intermediate of the tricarboxylic acid cycle by GDH or glutamine synthetase/glutamate synthase. Thus, these microorganisms share the same biosynthetic pathway for L-glutamic acid, and microorganisms mentioned above are encompassed within a single conception according to the present invention. Therefore, microorganisms belonging to the enteric bacteria other than species and strains mentioned above also fall within the scope of the present invention.

The microorganism of the present invention is a microorganism belonging to the enteric bacteria and having L-glutamic acid productivity. The term "having L-glutamic acid production ability" as herein used means to have ability for accumulating L-glutamic acid in culture medium during cultivation. This L-glutamic acid production ability may be either one possessed by a wild-type strain as its property, or one imparted or enhanced by breeding. Microorganism, which can be imparted L-glutamic acid productivity by being introduced gltA gene, may be also used. The microorganism belonging to the enteric bacteria and having the L-glutamic acid production ability include, for example, such microorganisms having increased activity of one or more enzymes catalyzing one or more reactions for the biosynthesis of L-glutamic acid, and such microorganisms having decreased activity of an enzyme catalyzing a reaction branching from the pathway for L-glutamic acid biosynthesis and producing a compound other than L-glutamic acid, or lacking the activity. The microorganism further includes those having increased activity of one or more enzymes catalyzing one or more reactions for the biosynthesis of L-glutamic acid, and decreased activity of an enzyme catalyzing a reaction branching from the pathway for L-glutamic acid biosynthesis and producing a compound other than L-glutamic acid, or lacking the activity.

The "coryneform bacteria" which can be a source for gltA gene being introduced into the enteric bacteria includes bacteria having been hitherto classified into the genus *Brevibacterium* but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform L-glutamic acid-producing bacteria include the followings.

Corynebacterium acetoacidophilum
Corynebacterium acetoglutamicum
Corynebacterium alkanolyticum
Corynebacterium callunae
Corynebacterium glutamicum
Corynebacterium lilium (Corynebacterium glutamicum)
Corynebacterium melassecola
Corynebacterium thermoaminogenes
Corynebacterium herculis
Brevibacterium divaricatum (Corynebacterium glutamicum)
Brevibacterium flavum (Corynebacterium glutamicum)
Brevibacterium immariophilum
Brevibacterium lactofermentum (Corynebacterium glutamicum)
Brevibacterium roseum
Brevibacterium saccharolyticum
Brevibacterium thiogenitalis
Brevibacterium album
Brevibacterium cerinum
Microbacterium ammoniaphilum Specifically, the following strains of these bacteria are exemplified:

Corynebacterium acetoacidophilum ATCC13870
Corynebacterium acetoglutamicum ATCC15806
Corynebacterium alkanolyticum ATCC21511
Corynebacterium callunae ATCC15991
Corynebacterium glutamicum ATCC13020, 13032, 13060
Corynebacterium lilium (Corynebacterium glutamicum) ATCC15990
Corynebacterium melassecola ATCC17965
Corynebacterium thermoaminogenes AJ12340(FERM BP-1539)
Corynebacterium herculis ATCC13868
Brevibacterium divaricatum (Corynebacterium glutamicum) ATCC14020
Brevibacterium flavum (Corynebacterium glutamicum) ATCC13826, ATCC14067
Brevibacterium immariophilum ATCC14068
Brevibacterium lactofermentum (Corynebacterium glutamicum) ATCC13665, ATCC13869
Brevibacterium roseum ATCC13825
Brevibacterium saccharolyticum ATCC14066
Brevibacterium thiogenitalis ATCC19240
Brevibacterium album ATCC15111
Brevibacterium cerinum ATCC15112
Microbacterium ammoniaphilum ATCC15354

A gltA gene derived from a coryneform bacterium can be obtained by isolating a DNA fragment which complement auxotrophy of a bacterium laking CS activity such as a mutant of a coryneform bacterium from the chromosome DNA of the coryneform bacterium. The nucleotide sequence of the gltA gene of the coryneform bacterium is made known (*Microbiology*, 140, 1817-1828 (1994)). Therefore the gltA gene can be obtained by PCR method using the chromosome DNA as a template and primers which are synthesized based on the nucleotide sequence. The primers are exemplified by oligonucleotides having nucleotide sequence shown in SEQ ID NOS: 1 and No. 2.

To introduce a CS gene derived from a coryneform bacterium into the microorganism belonging to enterobacteria, the CS gene may be cloned on an appropriate plasmid and the above starting parent strain which serves as a host may be transformed with the obtained recombinant plasmid. The number of copies of the CS gene (hereinafter abbreviated as "gltA gene") in the cell of the transformant is increased with the result of enhancement of CS activity.

While the plasmid is not particularly limited so long as it can autonomously replicate in a microorganism belonging to the enteric bacteria, examples of the plasmid include, for example, pUC19, pUC18, pBR322, pHSG299, pHSG298, pHSG399, pHSG398, RSF1010, pMW119, pMW118, pMW219, pMW218 and the like. Other than these plasmids, phage DNA vectors can also be used.

The introduction of the gltA gene can be realized by making the gltA gene present on the chromosome DNA of the above starting parent strain which serves as a host, preferably in multiple copies. To introduce the gltA gene into the chromosome DNA of the microorganism belonging to enterobacteria in multiple copies, a sequence present in the chromosome DNA in multiple copies such as repetitive DNA or inverted repeat present at a terminal region of a transposable element can be used. Alternatively, the gltA gene may be introduced into the chromosome DNA in multiple copies by inserting the gltA gene in a transposon and transposing the transposon. The number of copies of the gltA gene in the cell of the transformant increases, thereby enhancing CS activity.

Transformation may be performed in accordance with, for example, a method of D. A. Morrison (Methods in *Enzymology*, 68, 326 (1979)) or a method in which recipient cells are treated with calcium chloride to increase permeability for DNA (Mandel, M. and Higa, A., *J. Mol. Biol.*, 53, 159 (1970)).

The gltA gene which is to be introduced may have a promoter suitable for the cell of a microorganism belonging to enterobacteria, such as lac, trp, or $P_L$ in place of an inherent promoter of the gltA gene.

Techniques such as cloning of a gene, digestion and ligation of DNA and transformation method are described in Molecular Cloning, 2nd edition, Cold Spring Harbor Press (1989).

In the microorganism of the present invention, the activity of an enzyme which catalyzes the biosynthesis of L-glutamic acid other than CS may be enhancing in addition to the introduction of a gltA gene derived from a coryneform bacterium. Illustrative examples of the enzyme for catalyzing the biosynthesis of L-glutamic acid include glutamate dehydrogenase (GDH), glutamine synthase, glutamate synthase, isocitrate dehydrogenase, aconitate hydratase, phosphoenolpyruvate carboxylase (PEPC), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and the like.

The activity of an enzyme which catalyzes a reaction for generating a compound other than L-glutamic acid by branching off from the biosynthetic pathway of L-glutamic acid may be decreased or lost. Illustrative examples of the enzyme which catalyzes a reaction for generating a compound other than L-glutamic acid by branching off from the biosynthetic pathway of L-glutamic acid include α-ketoglutarate dehydrogenase (αKGDH), isocitrate lyase, phosphate acetyltransferase, acetate kinase, acetohydroximate synthase, acetolactate synthase, formate acetyltransferase, lactate dehydrogenase, glutamate decarboxylase, 1-pyrroline dehydrogenase and the like. Out of these enzymes, αKGDH is preferred.

The genes coding for PEPC and GDH can each be obtained from a chromosome DNA of the aforementioned microorganisms by isolating a DNA fragment complementing auxotrophy of a variant strain lacking the PEPC or GDH activity. Alternatively, because the nucleotide sequences of these genes of bacteria of the genus *Escherichia* or *Corynebacterium* have already been elucidated (*Biochemistry*, 22, 5243-5249 (1983); *J. Biochem*. 95, 909-916 (1984); *Gene*, 27, 193-199 (1984); *Mol. Gen. Genet*. 218, 330-339 (1989) and *Molecular Microbiology*, 6, 317-326 (1992)), the genes can be obtained by PCR using a primer synthesized based on each of the elucidated nucleotide sequences, and the chromosome DNA as a template.

In order to obtain such decrease or absence of enzyme activity as mentioned above in a microorganism belonging to the enteric bacteria, a mutation causing the decrease or absence of the enzyme activity can be introduced into a gene encoding the enzyme by a conventional mutagenesis technique or genetic engineering technique.

Examples of the mutagenesis technique include, for example, the method utilizing irradiation of X-ray or ultraviolet light, the method utilizing treatment with a mutagenic agent such as N-methyl-N'-nitro-N-nitrosoguanidine and the like. The site of gene to which a mutation is introduced may be a coding region encoding an enzyme protein, or an expression control region such as a promoter.

Examples of the genetic engineering technique include, for example, genetic recombination, genetic transduction, cell fusion and the like. For example, a drug resistance gene is inserted into a target gene to produce a functionally inactivated gene (disrupted gene). Then, this deletion type gene is introduced into a cell of a microorganism belonging to the enteric bacteria, and the target gene on a chromosome is replaced with the deletion type gene by homologous recombination (gene disruption).

Whether a microorganism has decreased activity of a target enzyme or lacks the activity, or degree of the decrease of the activity can be determined by measuring the enzyme activity of bacterial cell extract or purified fraction of a candidate strain, and comparing it with that of a wild-type strain. For example, the αKGDH enzymatic activity can be measured by the method of Reed et al. (L. J. Reed and B. B. Mukherjee, Methods in Enzymology 1969, 13, p. 55-61).

For some enzymes, a target mutant may be selected by phenotype of the mutant. For example, a mutant whose αKGDH activity is lost or decleased cannot grow or has a large decrease in its growth rate in a minimal medium containing glucose or a minimal medium containing acetic acid or L-glutamic acid as the only carbon source. However, normal growth is made possible by adding succinic acid or L-lysine, L-methionine and diaminopimelic acid to a minimal medium containing glucose under the same conditions. It is possible to carry out a screening for a mutant whose αKGDH activity is lost or decreased using this phenomenon as an index.

A method for producing a *Brevibacterium lactofermentum* strain lacking the αKGDH gene based on homogenous recombination is detailed in WO95/34672, and a similar method can be used for microorganisms belonging to the enteric bacteria.

Examples of the mutant strain that lack the αKGDH activity or have decreased activity thereof obtained as described above are *Enterobacter agglomerans* AJ13356 and *Klebsiella planticola* AJ13410. The strains *Enterobacter agglomerans* AJ13356 and *Klebsiella planticola* AJ13410 were deposited at the National Institute of Bioscience and Human-Technology, Agency of Industrial Science and Technology, Ministry of International Trade and Industry on Feb. 19, 1998 as accession numbers of FERM P-16645 and FERM P-16647, and then transferred to international deposits under the Budapest Treaty on Jan. 11, 1999, and received accession numbers of FERM BP-6615 and FERM BP-6617, respectively.

L-Glutamic acid can be produced and accumulated in a liquid culture medium by culturing the microorganism belonging to the enteric bacteria and being introduced gltA gene derived from coryneform bacteria in the medium.

The medium may be an ordinary nutrient medium containing a carbon source, nitrogen source, and inorganic salts, as well as organic nutrients such as amino acids, vitamins and the like, as required. It can be a synthetic medium or a natural medium. Any carbon sources and nitrogen sources can be used for the culture medium so long as they can be utilized by the microorganism to be cultured.

The carbon source may be a saccharide such as glucose, glycerol, fructose, sucrose, maltose, mannose, galactose, starch hydrolysates, molasses and the like. Further, an organic acid such as acetic acid and citric acid may also be used alone or in combination with other carbon sources.

The nitrogen source may be ammonia, ammonium salts such as ammonium sulfate, ammonium carbonate, ammonium chloride, ammonium phosphate, and ammonium acetate, nitrates and the like.

As organic trace nutrients, amino acids, vitamins, fatty acids, nucleic acids, materials containing them such as peptone, casamino acid, yeast extract, and soybean protein decomposition products and the like are used, and when an auxotrophic variant which requires an amino acid or the like for its growth is used, it is necessary to complement the nutrient required.

As the inorganic salt, phosphates, magnesium salts, calcium salts, iron salts, manganese salts and the like are used.

As for the culture conditions, cultivation is performed under aerobic condition at a temperature of 20-42° C. and a pH of 4-8. The cultivation can be continued for 10 hours to 4 days to accumulate a considerable amount of L-glutamic acid in the liquid culture medium.

After the completion of the cultivation, L-glutamic acid accumulated in the culture medium may be collected by a known method. For example, it can be isolated by a method comprising concentrating the medium after removing the cells to crystallize the product, ion exchange chromatography or the like.

According to the present invention, since a microorganism belonging to enterobacteria can be efficiently conferred L-glutamic acid productivity, it is assumed that higher productivity can be conferred on the microorganisms by conventionally known breeding techniques for coryneform L-glutamic acid producing bacteria. Studies on culture conditions and the like are expected to lead to the development of an inexpensive and efficient process for producing L-glutamic acid.

BEST MODE FOR CARRYING OUT THE INVENTION

The present invention will be explained more specifically with reference to the following examples.

(1) Construction of Plasmid having gltA Gene

Figure 1:
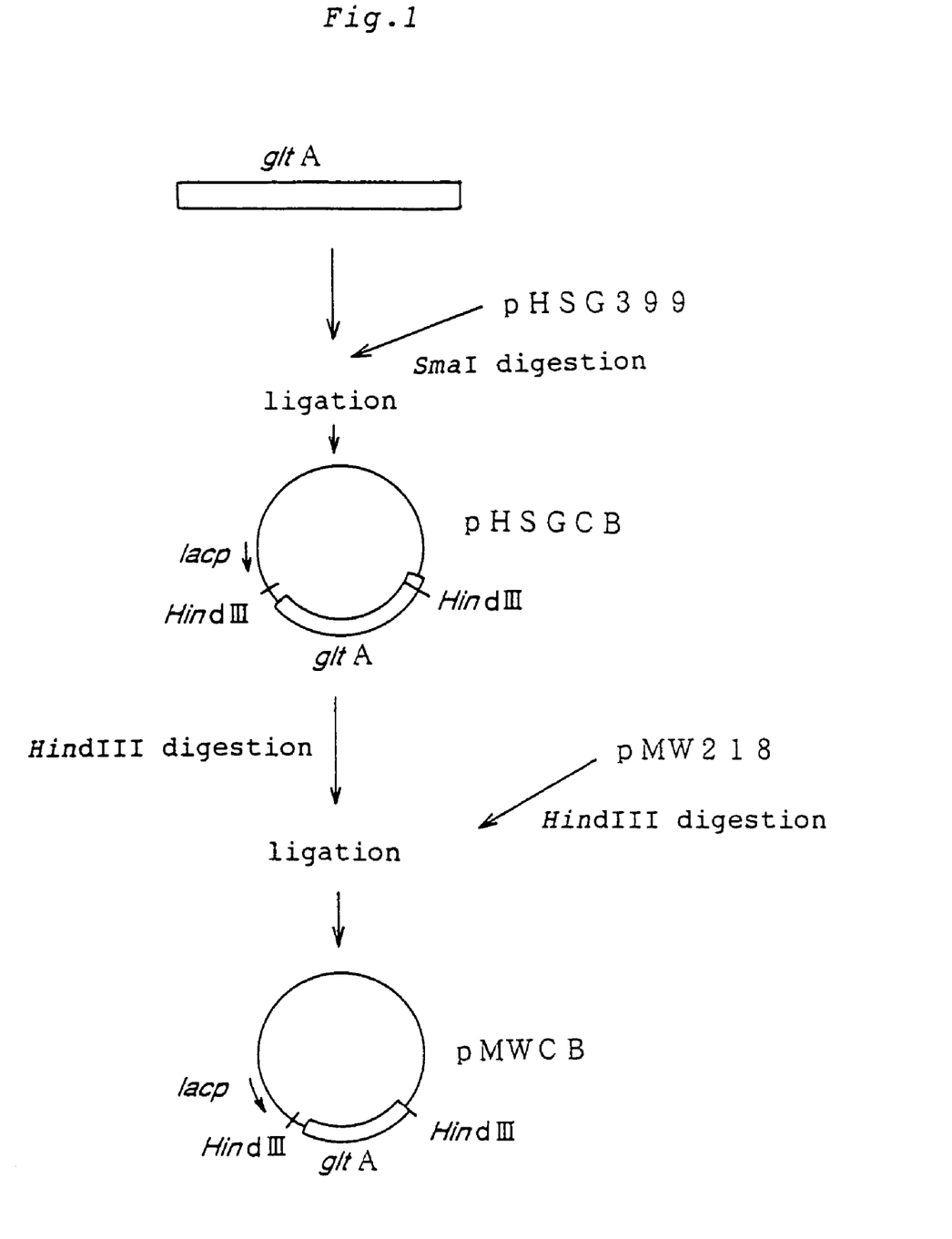
FIG. 1 shows the construction of a plasimd PMWCB having a gltA gene.

A plasmid having the gltA gene derived from *Brevibacterium lactofermentum* was constructed as follows. PCR was performed by using primers having the nucleotide sequences represented in SEQ ID NOS: 1 and 2 selected based on the nucleotide sequence of the gltA gene of *Corynebacterium glutamicum* (Microbiology, 1994, 140, 1817-1828), and a chromosome DNA of *Brevibacterium lactofermentum* ATCC 13869 as a template to afford a gltA gene fragment of about 3 kb. This fragment was inserted into the plasmid pHSG399 (purchased from Takara Shuzo) digested with SmaI to afford a plasmid PHSGCB (FIG. 1). Then, the pHSGCB was digested with HindIII, and an excised gltA gene fragment of about 3 kb was inserted into the plasmid pMW218 (purchased from Nippon Gene) digested with HindIII to afford a plasmid pMWCB (FIG. 1). Expression of the gltA gene by the resulting plasmid PMWCB was confirmed by determination of enzyme activity in the *Enterobacter agglomerans*. AJ13355 strain.

(2) Construction of Plasmid having gltA Gene Derived from *E. coli*

Figure 2:
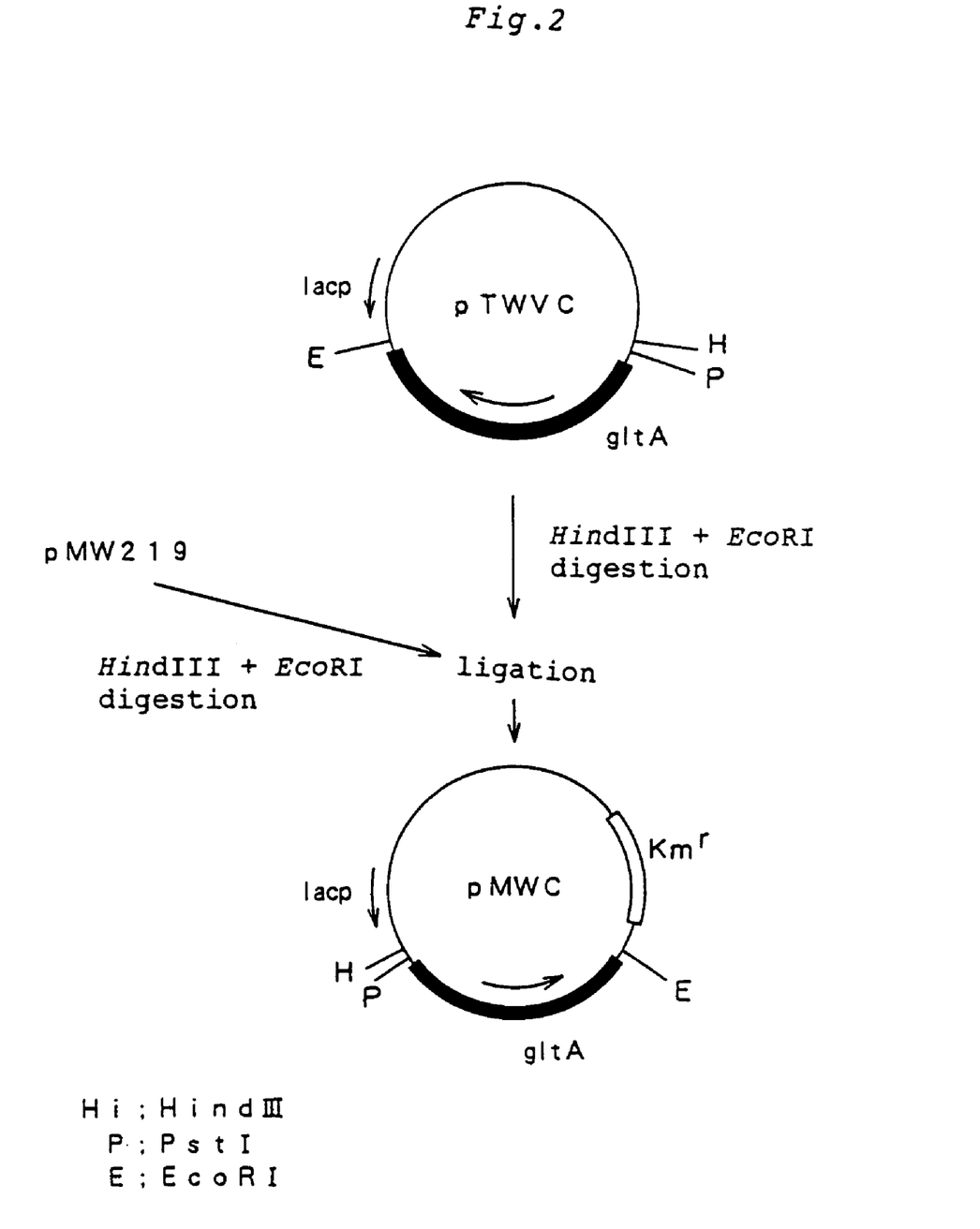
FIG. 2 shows the construction of a plasimd having a gltA gene.

As a control, a placmid having gltA gene derived from *Escherichia coli* was constructed as follows. The plasmid pTWVC having the gltA gene derived from *Escherichia coli* (WO97/08294) was digested with HindIII and EcoRI, and the resulting DNA fragment having the gltA gene was purified and collected, and introduced into the HindIII-EcoRI site of the plasmid pMW219 to afford a plasmid pMWC (FIG. 2). Expression of the gltA gene by the resulting plasmid pMWC was confirmed by determination of enzyme activity and complementation of auxotrophic strain of *E. coli* laking gltA gene.

(3) Introduction of gltA Gene into *Enterobacter agglomerans* and *Klebsiella planticola* and Production of L-Glutamic Acid The strains *Enterobacter agglomerans* AJ13355 and the *Klebsiella planticola* AJ13399 were transformed with pMWC or pMWCB. Each of the resulting transformants AJ13355/pMWC, AJ13355/pMWCB, AJ13399/pMWC and AJ13399/pMWCB and the parent strains were inoculated into 500 ml-volume flask containing 20 ml of culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, and 30 g/L calcium carbonate, and cultured at 37° C. for 15 hours with shaking. After the cultivation was completed, L-glutamic acid accumulated in the culture medium and residual glucose were measured. The results are shown in Table 1.

TABLE 1

| | Accumulated amount of L-glutamic acid | |
|---|---|---|
| Bacterial strain | Accumulated amount of L-glutamic acid (g/L) | Residual amount of Glucose (g/L) |
| AJ13355 | 0 | 0 |
| AJ13355/pMWC | 0.01 | 6.0 |
| AJ13355/pMWCB | 0.78 | 28.5 |
| AJ13399 | 0 | 0 |
| AJ13399/pMWC | 2.85 | 0 |
| AJ13399/pMWCB | 4.71 | 0 |

L-glutamic acid productivity was observed in both *Enterobacter* agromellans AJ13355 and *Klebsiella planticola* AJ13399 by introducing a gltA gene. The accumulation of L-glutamic acid is more marked when a gltA gene derived from *Brevibacterium lactofermentum* is introduced than when a gltA gene derived from *Escherichia coli* is introduced. A great amount of glucose remains in the case of the AJ13355/pMWCB without being consumed under the above conditions. When culture is carried out until all glucose is consumed, it is assumed that about 1.5 to 2 g/l of L-glutamic acid can be accumulated.

There was not seen a marked difference in the copy number of plasmid between AJ13355/pMWC and AJ13355/pMWCB, and between AJ13399/pMWC and AJ13399/pMWCB.

What is claimed is:

1. An isolated microorganism belonging to enterobacteria selected from the group consisting of the genus *Enterobacter, Pantoea, Klebsiella, Erwinia* and *Serattia* and having L-glutamic acid productivity which is transformed by a polynucleotide sequence encoding a citrate synthase obtained from *Corynebacterium glutamicum* or *Brevibacterium lactofermentum*,
wherein the transformed microorganism has enhanced L-glutamic acid productivity as compared to the untransformed microorganism.

2. The microorganism of claim 1, which is transformed by a polynucleotide sequence encoding a citrate synthase obtained from *Corynebacterium glutamicum*.

3. The microorganism of claim 1, which is transformed by a polynucleotide sequence encoding a citrate synthase obtained from *Brevibacterium lactofermentum*.

4. The microorganism of claim 1, wherein the microorganism belonging to enterobacteria is a bacterium belonging to the genus *Enterobacter*.

5. The microorganism of claim 4, wherein the microorganism is *Enterobacter agglomerans*.

6. The microorganism of claim 1, wherein the microorganism belonging to enterobacteria is a bacterium belonging to the genus *Klebsiella*.

7. The microorganism of claim 6, wherein the microorganism is *Klebsiella planticola*.

8. The microorganism of claim 1, wherein the polynucleotide is obtained from *Corynebacterium glutamicum* or *Brevibacterium lactofermentum* chromosomal DNA by the polymerase chain reaction using oligonucleotide primers of SEQ ID NO: 1 and SEQ ID NO: 2.

9. The microorganism of claim 1, wherein the microorganism belongs the genus *Pantoea*.

10. The microorganism of claim 1, wherein the microorganism belongs the genus *Klebsiella*.

11. The microorganism of claim 1, wherein the microorganism belongs the genus *Erwinia*.

12. The microorganism of claim 1, wherein the microorganism belongs the genus *Serattia*.

13. A process for producing L-glutamic acid, comprising:
culturing the microorganism of claim 1 in a liquid medium to produce and accumulate L-glutamic acid in the medium and collecting the L-glutamic acid from the medium.

14. The process of claim 13, wherein the enterobacteria is of the genus *Enterobacter* or *Klebsiella*.

15. The process of claim 13, wherein the enterobacteria is *Enterobacter agglomerans* or *Klebsiella* planticola.

16. A process for producing L-glutamic acid, comprising:
isolating a polynucleotide sequence encoding a citrate synthase obtained from a coryneform bacterium, wherein the polynucleotide is obtainable by the polymerase chain reaction using oligonucleotide primers of SEQ ID NO: 1 and SEQ ID NO: 2;
transforming an enterobacterium with said isolated polynucleotide;
culturing said enterobacterium in a liquid medium to produce and accumulate the L-glutamic acid, wherein the transformed enterobacterium has enhanced L-glutamic acid productivity as compared to the untransformed enterobacterium; and
collecting the L-glutamic acid produced.

17. The process of claim 16, *coryneform* wherein the bacterium is *Corynebacterium glutamicum* or *Brevibacterium lactofermentum*.

18. The process of claim 16, wherein the enterobacterium is of the genus *Enterobacter* or *Klebsiella*.

19. The process of claim 16, wherein the enterobacterium is *Enterobacter agglomerans* or *Klebsiella planticola*.

* * * * *

UNITED STATES PATENT AND TRADEMARK OFFICE
CERTIFICATE OF CORRECTION

PATENT NO. : 7,247,459 B1  Page 1 of 1
APPLICATION NO. : 09/419611
DATED : July 24, 2007
INVENTOR(S) : Hiroshi Izul et al.

It is certified that error appears in the above-identified patent and that said Letters Patent is hereby corrected as shown below:

Cover page, (56) References Cited,
Foreign Patent Documents " JP   32-9393 S   12/1957 "
should read -- JP   32-9393 S   11/1957 --;
" WO   0 670 370   9/1995 "
should read -- EP 0 670 370   9/1995 --.

Column 14, lines 42 and 43, " coryneform wherein the bacterium is "
should read -- wherein the coryneform bacterium is --.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO.        : 7,247,459 B1                                        Page 1 of 1
APPLICATION NO. : 09/419611
DATED             : July 24, 2007
INVENTOR(S)       : Hiroshi Izui et al.

It is certified that error appears in the above-identified patent and that said Letters Patent is hereby corrected as shown below:

Cover page, (56) References Cited,
   Foreign Patent Documents "JP   32-9393 S   12/1957"
     should read -- JP   32-9393 S   11/1957 --;
       "WO   0 670 370   9/1995"
    should read -- EP 0 670 370   9/1995 --.

Column 14, lines 42 and 43, "coryneform wherein the bacterium is"
    should read -- wherein the coryneform bacterium is --.

This certificate supersedes the Certificate of Correction issued December 11, 2007.

Signed and Sealed this

Twelfth Day of February, 2008

JON W. DUDAS
*Director of the United States Patent and Trademark Office*